United States Patent [19]

Engle

[11] 4,095,031

[45] June 13, 1978

[54] PERFUMED COPOLYMERS OF ETHYLENE AND POLAR MONOMER

[75] Inventor: Edward Jacob Engle, Hockessin, Del.

[73] Assignee: Polak's Frutal Works, Inc., Middletown, N.Y.

[21] Appl. No.: 766,631

[22] Filed: Feb. 8, 1977

[51] Int. Cl.² ............................................... C08K 5/00
[52] U.S. Cl. .......................................... 526/1; 252/522
[58] Field of Search ................ 424/78, 81, 83; 526/1, 526/343; 252/522

[56] References Cited

U.S. PATENT DOCUMENTS

| | | | |
|---|---|---|---|
| 2,397,260 | 3/1946 | Hanford | 526/343 |
| 3,505,432 | 4/1970 | Neuwald | 526/1 |
| 3,553,296 | 1/1971 | Gaeckel | 252/522 |
| 3,567,119 | 3/1971 | Wilbert | 424/78 |

*Primary Examiner*—Paul R. Michl
*Attorney, Agent, or Firm*—William S. Alexander

[57] ABSTRACT

Perfumed composites of ethylene and polar monomer copolymers, such as vinyl acetate and ethyl acrylate, are disclosed. Shaped bodies prepared from such composites faithfully retain the fragrance of the perfume oil for periods up to a year and more.

3 Claims, No Drawings

PERFUMED COPOLYMERS OF ETHYLENE AND POLAR MONOMER

This invention relates to clear, perfumed thermoplastic resins suitable for the preparation of shaped objects from which the perfume odor emanates over a period of time at substantially a stable level.

A number of thermoformable perfumed compositions have been proposed heretofore. In particular, high and low density polyethylene and polyvinyl chloride perfumed molding powers have been sought. With the polyethylenes, however, only limited success has been obtained due to the almost total incompatibility of the perfume oil and the polymer, leading to exudation of the perfume from the polymer matrix. Moreover, the high melting point and consequent high molding temperatures required of some polyethylenes are so high as to cause damage to the perfume oil incorporated therein. With polyvinyl chloride it has apparently been found necessary to incorporate a filler to carry the perfume oil.

In accordance with this invention, thermoplastic shaped bodies are provided which faithfully retain the odor of the perfume material contained therein and from which the perfume oil does not exude to a significant extent. These improved and highly useful shaped bodies are prepared by using as the resin phase a copolymer of ethylene and a polar vinyl comonomer. Specifically, the invention is a shaped thermoplastic resin body consisting essentially of a copolymer of ethylene and a polar vinyl comonomer and about 1 to 30% by weight of a perfume oil, based on the weight of the resin.

To be used successfully in perfumed plastics, a resin must have a low processing temperature so that more volatile components of the perfume are not lost during processing. It should be sufficiently compatible with perfume oils so that the oil does not exude so rapidly as to wet the surface of the shaped body but it should have a degree of incompatibility that will permit the odor of the perfume to emanate from the body of plastic. On the practical side, the resin must be sufficiently inexpensive and durable to permit its use broadly in everyday, disposable items. In accordance with this invention, it has been found that the ethylene—polar vinyl monomer copolymers and terpolymers are excellently suited to the preparation of thermoformed resin bodies on each of the counts listed.

The preferred copolymers are those containing about 6 to 60% by weight of the polar vinyl comonomer, e.g., ethylene—vinyl acetate, ethylene—ethyl acrylate, ethylene—methyl acrylate, ethylene—vinyl alcohol, ethylene—butyl acrylate and ethylene—acrylic acid. The preferred copolymers are ethylene—vinyl acetate with about 9 to 60% vinyl acetate and ethylene—ethyl acrylate with about 6 to 18% ethyl acrylate.

These resins are normally solid, relatively low molecular weight materials. They are moldable at relatively low temperatures, i.e., less than about 175° C., by any of the common molding techniques. Thus, they can be either compression or injection molded without reaching temperatures sufficient to damage the perfume components. In addition, they are themselves relatively odorless.

Resins of the type disclosed are commercially available in molding powder form. For example, ethylene—vinyl acetate copolymers are marketed by the Du Pont Company under the trade name "Elvax", by Arco Polymers under the trade name "Dylan" and by Exxon under the trade name "Dexxon". Ethylene—ethyl acrylate copolymers are marketed by Union Carbide under the trade name "EEA Resins".

The process of making the perfume resin bodies of this invention comprises heating the resin until it is sufficiently molten to be free-flowing. As suggested previously, this is usually between about 100° and 175° C. for these resins. The perfume oil is added to the molten resin and blended through the mass by stirring or other mechanical agitation until a uniform mixture is obtained. A two-mill roll is suited for this purpose. Since the resin is thermoplastic, no solvents are required for the blending. The perfumed mass can be extruded and reduced to molding powder at this point by conventional methods or it can be molded into the desired shape prior to cooling.

Exposure to the melting, blending and molding temperatures of these resins does not negatively affect the perfurm odor. Molding powder produced as described in the preceding paragraph can be processed through injection or compression molding and the original odor will be faithfully retained. In fact, the fragrance will be faithfully retained for several months' storage and in many cases up to a year or more even when the resin body is exposed to the atmosphere.

Perfume oils suitable for the present invention include substantially any of the conventional fragrance materials. These are complex mixtures of volatile compounds including esters, ethers, aldehydes, alcohols, unsaturated hydrocarbons, terpenes such as are well known to those skilled in the fragrance art. Specific perfume oils are musks, rose oil, honeysuckle oil, pine oil, jasmin or oak moss, for example. Their use as to type and proportion is limited only by their solubility in the resin.

The proportion of perfume oil to resin can vary from small but effective amounts on the order of about 1% of the weight of resin up to about 30%. In general, it is preferred to use about 10% to 15% based on the weight of the resin, which is an optimum value balancing the proportion of perfume oil in the product against the time period over which the article emits the odor and against the tendency of the perfume to "oil out".

The perfumed resin of the present invention can be formed into a wide variety of useful objects such as jewelry, e.g., pins and brooches, decorative castings such as artificial flowers, combs, room fresheners, sachets and many others. It can also be employed as a coating on a substrate.

EXAMPLE 1

An ethylene—ethyl acrylate copolymer containing 6% by weight of ethyl acrylate was compounded with perfume in a 3.25 in. twin screw extruder. The temperature across the extruder varied from 320° in the first zone to 300° F. in the fourth zone. A fresh floral mossy perfume oil was pumped into the extruder through the vent to give perfumed polymer strands that were extruded into ice water and chopped into pellets. By thermogravimetric analysis it was determined that the product contained about 10.5% perfume.

The formulation thus prepared was injected molded at 320° F. to form hair combs of 17 × 4 cm. dimensions, weighing 11.8 grams. The odor of these combs was judged to be not materially different from that of the perfume added thereto. The odor level remained substantially the same after one year in storage with no evidence of oiling out on the polymer surface.

EXAMPLE 2

Additional portions of the ethylene—ethyl acrylate copolymer were compounded with the perfume oil using a temperature profile ranging from 350° in the first zone to 320° F. in the fourth zone and 320° F. at the die. By thermogravimetric analysis these were determined to contain 11.5 and 11% perfume. The odor of the perfume was faithfully retained even after several months' storage, and there was no evidence of oiling out.

EXAMPLE 3

Three portions of ethylene—ethyl acrylate copolymer containing about 18% ethyl acrylate were blended with perfume in the manner described in Example 1 above. The extruder temperature profile ranged from 320° in the first zone to 300° F. in the fourth zone and 310° F. at the die.

The perfume content was 10.5%, 17%, and 19%, respectively. Each of these faithfully retained the perfume odor and continued to do so with little or no oiling out over a period of several months.

EXAMPLE 4

Two specimens of ethylene—vinyl acetate (VA) copolymer, containing 25% and 18%, respectively, of vinyl acetate were compounded with about 15% by weight of a fruity oriental perfume oil on a two-roll mill at 200° F. The blended material was compression molded into flat plaques. Molding temperature was 260° F. for the 25% VA materials, 240° F. for the 18% VA material.

In each instance the molded plaque exhibited the odor of the original perfume substantially unchanged for several months. There was no oiling out of the perfume on the polymer surface.

EXAMPLE 5

Specimens of ethylene—ethyl acrylate copolymer containing 18% of ethyl acrylate were compounded with about 10% by weight of the fresh floral mossy perfume oil on a two-roll mill at 250° F. These were injection molded into flat plaques at 320° F.

In the same manner specimens of ethylene—ethyl acrylate copolymer containing 8% of ethyl acrylate were compounded with 10% perfume at 275° F. and injection molded at 320°–350° F.

In each case, the moldings exhibited the original perfume odor faithfully over an extended period of time without oiling out on the plastic surface.

EXAMPLE 6

A specimen of low density polyethylene was compounded on a two-roll mill at 250° F. with about 10% by weight of the perfume employed in Example 5. This material was compression molded into a plaque at 265° F. The perfume odor was substantially unchanged, but the surface of the plaque was oily and wet to the touch.

What I claim and desire to protect by Letters Patent is:

1. A thermoplastic resin body consisting essentially of a thermoplastic copolymer of ethylene and about 6 to 60% by weight of a polar vinyl monomer selected from the class consisting of
   (a) vinyl acetate;
   (b) ethyl acrylate;
   (c) methyl acrylate;
   (d) butyl acrylate; and
   (e) acrylic acid and about 1 to 30% by weight of perfume oil.

2. The thermoplastic resin body of claim 1 wherein the thermoplastic copolymer is comprised of ethylene and about 6 to 18% by weight ethyl acrylate.

3. The thermoplastic resin body of claim 1 wherein the thermoplastic copolymer is comprised of ethylene and about 9 to 60% by weight of vinyl acetate.

* * * * *